United States Patent [19]

Lee et al.

[11] Patent Number: 5,795,591
[45] Date of Patent: Aug. 18, 1998

[54] OSMOTIC DRUG DELIVERY DEVICES WITH HYDROPHOBIC WALL MATERIALS

[75] Inventors: Eun Soo Lee, Redwood City; Scott A. Bura, Palo Alto; Su Il Yum, Los Altos; Patrick S.-L. Wong, Palo Alto; Felix Theeuwes, Los Altos, all of Calif.

[73] Assignee: ALZA Corporation, Palo Alto, Calif.

[21] Appl. No.: 299,867

[22] Filed: Sep. 1, 1994

Related U.S. Application Data

[63] Continuation of Ser. No. 775,635, Oct. 10, 1991, abandoned.
[51] Int. Cl.$^6$ .................................................. A61K 9/26
[52] U.S. Cl. .................. 424/473; 424/408; 424/424; 424/433; 424/438; 604/890.1; 604/891.1; 604/892.1
[58] Field of Search .................... 424/408, 424–426, 424/428, 433–436, 438, 451, 452, 465, 470, 473, 485, 486, 488, DIG. 7; 604/890.1, 891.1, 892.1

[56] References Cited

U.S. PATENT DOCUMENTS

| | | | |
|---|---|---|---|
| 3,991,766 | 11/1976 | Schmitt et al. | 128/335.5 |
| 4,034,758 | 7/1977 | Theeuwes | 424/427 |
| 4,093,708 | 6/1978 | Zaffaroni et al. | 424/15 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,135,514 | 1/1979 | Zaffaroni | 924/427 |
| 4,220,153 | 9/1980 | Dresback | 424/438 |
| 4,235,236 | 11/1980 | Theeuwes | 128/260 |
| 4,327,725 | 5/1982 | Cortese et al. | 128/260 |
| 4,400,374 | 8/1983 | Cardarelli | 424/78 |
| 4,552,752 | 11/1985 | Amick | 424/21 |
| 4,656,057 | 4/1987 | Amick | 427/245 |
| 4,751,071 | 6/1988 | Magruder et al. | 424/467 |
| 4,783,337 | 11/1988 | Wong et al. | 424/468 |
| 4,968,507 | 11/1990 | Zentner et al. | 424/465 |
| 5,008,112 | 4/1991 | DePrince et al. | 424/468 |
| 5,145,945 | 9/1992 | Tang et al. | 528/370 |
| 5,368,863 | 11/1994 | Eckenhoff et al. | 424/473 |
| 5,516,527 | 5/1996 | Curatolo | 424/461 |

FOREIGN PATENT DOCUMENTS

| | | |
|---|---|---|
| 0040457 | 11/1981 | European Pat. Off. . |
| 0089548 | 9/1983 | European Pat. Off. . |
| 0337613 | 10/1989 | European Pat. Off. . |
| 0373867 | 6/1990 | European Pat. Off. . |

OTHER PUBLICATIONS

Yolles, S., et al., Polymer News 1(4/5):9–15 (1971).
Kulkarni, R.K., et al., J. Biomed. Mater. Res. 5:169–181 (1971).
Wise, D.L., Acta Pharm Suecica 13 (suppl.):34 (1976).

*Primary Examiner*—Neil S. Levy
*Attorney, Agent, or Firm*—Steven F. Stone; Mary Ann Dillahunty

[57] ABSTRACT

Osmotically driven drug delivery devices with walls of porous hydrophobic material as the sole diffusion-limiting wall component are disclosed. Despite pores which are considerably larger than the molecular dimensions of osmotically active species in the interior of the device, despite pores which by their hydrophobic character do not permit the passage of liquid water, and despite the absence of a cellulosic semi-permeable membrane, the devices absorb water by osmosis without loss of the osmotically active species, and function in a manner analogous to osmotic pumps of the prior art. By permitting the use of hydrophobic substances as the wall material, the invention permits the device to be constructed entirely from biodegradable materials.

12 Claims, 4 Drawing Sheets

OSMOTIC DRUG DELIVERY DEVICES WITH HYDROPHOBIC WALL MATERIALS

This application is a continuation of application Ser. No. 07/775,635, filed Oct. 10, 1991, now abandoned and benefit of the filing date of said earlier filed application is claimed under 35 U.S.C. § 120.

This invention lies in the field of controlled—or sustained—release drug delivery systems. More particularly, this invention relates to osmotic drug delivery systems, which are encapsulated drugs gradually released through an orifice in the capsule by internal pressure resulting from the imbibition of fluid by the capsule from a surrounding physiological medium.

BACKGROUND OF THE INVENTION

Osmotic drug delivery capsules, commonly referred to as "osmotic pumps," function by virtue of walls which selectively pass water from a biological environment such as the gastro-intestinal tract into the capsule reservoir. This imbibition of water occurs as the result of osmotic pressure due to the osmotic activity of the drug or of a water-attracting agent in the capsule interior, or both, depending on the location of these species in the capsule reservoir and the structure of the reservoir. Because the capsule wall's structure does not allow expansion of the capsule, the drug must leave the interior of the capsule through a small orifice at the same rate that water enters the capsule by osmosis.

The terms "osmotically effective" and "osmotically active" are used in the literature to characterize the species in the capsule which drive the osmotic flow. Certain agents of this type are termed "osmagents," which denotes water-soluble compounds to which the capsule wall is not permeable. The drug itself may be one of these species. Osmotically effective agents which are polymeric species are termed "osmopolymers," which term denotes water-swellable polymers. Osmagents and osmopolymers may be used individually in a capsule or they may be present as a mixture of the two. In cases where the osmotically active agent is separated from the beneficial agent by a movable partition or piston, the osmotically active agent and the compartment in which it resides may be referred to as an "osmotic engine."

Representative literature on osmotic pumps of this nature includes Theeuwes, U.S. Pat. No. 4,111,201, Theeuwes, U.S. Pat. No. 4,111,202, and Theeuwes, U.S. Pat. No. 4,111,203, all issued Sep. 5, 1978, Cortese, et al., U.S. Pat. No. 4,327,725, issued May 4, 1982, Magruder, et al., U.S. Pat. No. 4,751,071, issued Jun. 14, 1988, and Wong, et al., U.S. Pat. No. 4,783,337, issued Nov. 8, 1988.

According to the disclosures of these patents, the selective permeability of the capsule wall is achieved by the use of semi-permeable membranes generally made of cellulosic materials such as cellulose acetates, acylates, alkanylates and aroylates. Included in the disclosures are capsules in which the wall is formed entirely of these cellulosic materials, as well as capsules in which the wall is a laminate of cellulosic and microporous laminae. Microporous laminae are included in these laminates to provide structural support to the relatively thin and fragile cellulosic laminae. The advantage of such a laminate is that it permits the use of a very thin layer of cellulose, thereby offering a high water absorption rate while still preventing the passage of the other components of the system. The microporous lamina in these disclosures is permeable to all components of the system with the exception of certain osmopolymers and certain drugs, depending on the pore size of the microporous material.

The osmotic mechanism described in these disclosures imposes certain limitations on the materials which can be used to form the capsule walls.

Since osmosis requires the passage of water through the capsule walls by diffusion, one limitation is the need for a continuous aqueous liquid diffusion path across the capsule wall. For walls which include microporous lamina, this means that the interior pore surfaces of the microporous lamina must be wettable by water, and the microporous material must therefore be hydrophilic. This limits the choice of materials by excluding hydrophobic materials, many of which would otherwise be desirable for certain properties which they alone possess. Certain hydrophobic materials, for example, are biodegradable.

Another limitation is the need for a semi-permeable material. Whether used as the sole component of the wall or as a component of a laminated wall, this as well limits the choice of materials. In addition, the semi-permeable material must be thin enough to achieve a water permeation rate which is sufficiently high for effective drug delivery, yet thick enough to provide a structure sufficiently sturdy to withstand the pressures and forces encountered both during and after implantation or ingestion of the capsule. Bursting of the capsule under high osmotic pressure will cause premature release of the drug, impairing the ability of the capsule to deliver the drug at a steady rate or in a sustained manner over a period of time.

A third limitation resides in the balance between function and effect in the microporous lamina. If the microporous lamina itself is to serve as a means of preventing escape of the drug, osmagent or osmopolymer, thereby contributing to the effect of the semi-permeable membrane, the pores of the microporous lamina must be of a smaller diameter than the molecular dimensions of the species the microporous lamina is intended to block. Microporous lamina with pores this small, however, will decrease the rate at which water will diffuse into the capsule, thereby limiting the rate at which the capsule can deliver the drug to the surrounding medium. If, on the other hand, one seeks to avoid any effect of the microporous lamina on the water absorption rate by increasing the pore size, the pores will be too large for the lamina to function as a molecular sieve, and the entire burden of preventing escape of internal capsule materials will be borne by the semi-permeable membrane.

In addition to the patents cited above, other literature of possible relevance to this invention are Schmitt, et al., U.S. Pat. No. 3,991,766, issued Nov. 16, 1976; Yolles, S., et al., *Polymer News* 1(4/5): 9–15 (1971); Kulkarni, R. K., et al., *J. Biomed. Mater. Res.* 5: 169–181 (1971); and Wise, D. L., *Acta Pharm. Suecica* 13(suppl.): 34 (1976). These documents disclose the use of poly(lactic acid), poly(glycolic acid) and copolymers of lactic acid and glycolic acid in controlled release drug delivery systems. The possible relevance of these materials will be evident from the description which follows.

These and other limitations and disadvantages of known osmotic drug delivery systems are addressed by the present invention.

SUMMARY OF THE INVENTION

A sustained-release drug delivery device similar in form to the osmotic devices of the prior art, and similarly operating by selectively imbibing water in a continuous manner to force the drug out through an orifice, but which avoids the use of either conventional semi-permeable membranes or hydrophilic wall materials, has now been developed. In accordance with this invention, a porous hydrophobic material replaces both the semi-permeable membrane and the microporous hydrophilic material. The porous hydrophobic material alone serves both as the rate-limiting component of the wall in terms of water permeation and as the component preventing outward diffusion of the encapsulated materials prior to implantation or ingestion of the capsule in a living animal.

One surprising and unexpected feature of capsules with walls in accordance with this invention is the ability of such capsules to draw water from the outside in despite the lack of wetting of the pores, and thus despite the presence of discontinuities in the liquid diffusion path across the capsule wall due to the gas residing in the pores. Surprisingly, the capsules function in the same manner as those of the prior art, driving the encapsulated drug out in a continuous and substantially steady manner over an extended period of time. In fact, this invention permits one to control the drug delivery rate directly by controlling both the diameter of the pores and the number of the pores per unit external surface area of the wall.

Another surprising and unexpected feature of capsules with walls in accordance with this invention is their ability to prevent the passage of osmagents and osmopolymers from the capsule interior despite the lack of a conventional cellulose-based semi-permeable membrane, and without the need to control the pore size to a diameter smaller than the diameter of the species whose passage is prevented. This is particularly unexpected when osmagents such as simple inorganic salts are used whose molecular dimensions are much smaller than the cross sections of the pores. For those capsules in which the drug as well is in contact with the porous hydrophobic wall, the wall similarly prevents passage of the drug.

Accordingly, a single material in the wall construction serves several functions:

(a) it permits the passage of water into the capsule interior in a continuous manner to provide drug delivery at a steady rate;

(b) it controls the rate at which water will pass into the capsule interior; and (c) it excludes non-volatile materials residing in the capsule from passage through the capsule wall.

A major advantage of the present invention is that it renders possible the construction of the capsule from biodegradable polymers. Exemplary biodegradable polymers are polymers of d,l-lactic acid, polymers of glycolic acid, and copolymers of lactic and glycolic acids, all of which are hydrophobic and accordingly beyond either the teachings of the prior art relating to osmotically driven drug delivery devices, or the mechanistic theories of osmosis on which these teachings are based. Continuous walls of these polymers have very low water permeability whereas porous walls are permeable in accordance with the invention, particularly when in a physiological environment, the permeability being selective to water relative to non-volatile water-soluble or hydrophilic species regardless of the molecular dimensions of such species.

DETAILED DESCRIPTION OF THE INVENTION AND PREFERRED EMBODIMENTS

Figure 1:
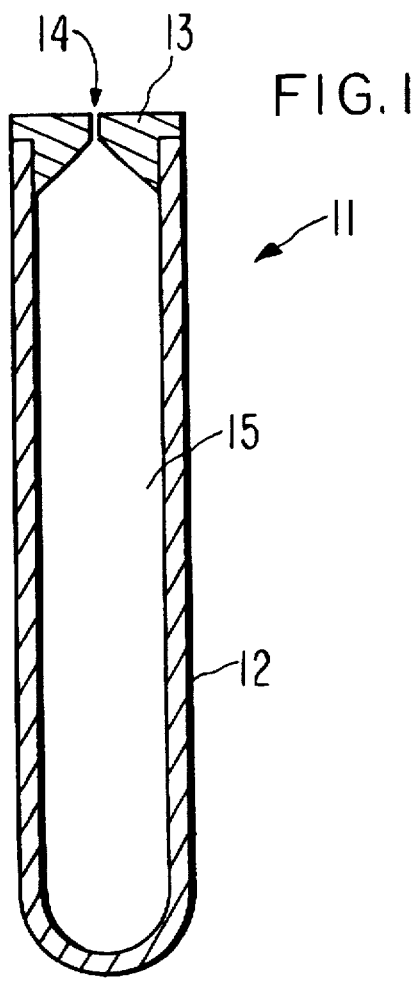
FIG. 1 is a cross section of an osmotic drug delivery device representing one example of a means of implementing the present invention.

Materials for the capsule wall in accordance with the present invention extend to all materials whose surfaces are not wetted by water or by the aqueous fluids which the capsule will encounter upon ingestion or implantation in a biological environment. The porous walls of the capsule will therefore not fill with water upon contact nor will they permit water to pass as a liquid through the capsule walls. This includes homogeneous materials with non-wetting surface characteristics, as well as materials containing a surface coating of a non-wetting substance.

The non-wetting materials of the invention include hydrophobic materials in general, particularly hydrophobic polymers. As indicated above, hydrophobic materials of particular interest are hydrophobic biodegradable polymers. Examples of hydrophobic biodegradable polymers for use in the practice of this invention are poly-beta-hydroxybutyrate, poly-beta-hydroxyvalerate, poly-beta-hydroxybutyrate-beta-hydroxyvalerate, polyanhydrides, polyorthoesters, and polymers and copolymers of hydroxycarboxylic acids. Prime examples of polymers and copolymers of hydroxycarboxylic acids are polymers of d-lactic acid, l-lactic acid, d,l-lactic acid, glycolic acid, and methylethylglycolic acid, copolymers of lactic and glycolic acids, and copolymers of caprolactone and lactic acid. Polymers of d,l-lactic acid and copolymers of lactic and glycolic acids are preferred. Examples of polymers which are hydrophobic but not biodegradable, also for use in the practice of this invention, are polyethylene, polypropylene, polytetrafluoroethylene (Teflon), polycarbonate, polystyrene, polyvinylchloride, poly(ethylene-terephthalate), polysulfones, polyacrylonitrile, polymethylmethacrylate, polyvinylidene chloride, polyvinylidene fluoride, polyamides (such as 6-nylon, 610-nylon, 612-nylon, 12-nylon, and 11-nylon), aromatic polyamides, and polyimides.

The wall material in accordance with the invention will be porous, forming a pore network which is sufficiently interconnected and open at the wall surface to permit passageways for vapors to pass through the wall. The pore diameter is not critical and may vary widely. The choice however of an optimum pore size range will depend on the wall thickness and overall surface area and the desired rate of water imbibition through the wall, as well as considerations encountered in the manufacture of the wall, notably the means of forming the pores and the materials used.

In most applications, the average pore diameter will fall within the range of from about 0.01 micron to about 1000 microns. Preferred ranges are from about 0.1 micron to about 500 microns, from about 3 microns to about 300 microns, and most preferably from about 30 microns to about 100 microns. The term "average pore diameter" as used herein refers to the effective diameter of the passages connecting the voids in the wall material.

Wall materials with pores within these size ranges are made by techniques well known among those skilled in the art of porous polymers and membranes. The pores may be formed in a preformed non-porous wall by etching or nuclear tracking. An alternative method involves stretching of the polymer at low or high temperatures until pores are formed. As a further alternative method, the pores may be formed during formation of the wall by first forming a solution of the uncured polymer, cooling the solution below its freezing point to crystallize the solvent, lyophilizing the crystallized solvent and curing the polymer, leaving gaps in the regions occupied by the solvent crystals.

A preferred method of forming the pores is one which also occurs during formation of the wall, but involves the use of a pore forming agent other than a solvent. The pore forming agent used in this method is either a solid, a semi-solid or a viscous liquid, and may be organic or inorganic. The pore forming agent is combined with the polymeric wall material while the polymer is in a liquid form, either prior to cure or subsequent to cure but dissolved in a solvent. The pore forming agent is then retained in the polymeric material as the wall is being formed and, if necessary, the polymer cured. The agent is then removed from the wall by dissolving, extracting, eroding or leaching, without any chemical change to the remaining polymer. After the agent is removed, the polymer is thoroughly vacuum dried to remove all traces of liquid, leaving open, interconnected, air-filled pores.

Pore forming agents capable of use in this method include a wide range of materials. Examples are alkali metal salts such as sodium chloride, sodium bromide, potassium chloride, potassium sulfate, potassium phosphate, sodium benzoate, sodium acetate, sodium citrate, and potassium nitrate, alkali earth metal salts such as calcium phosphate and calcium nitrate, transition metal salts such as ferric choride, ferrous sulfate, zinc sulfate, cupric chloride, manganese fluoride, and manganese fluorosilicate. Further examples are monosaccharides, oligosaccharides and polysaccharides, notably sucrose, glucose, fructose, mannose, galactose, fucose, rhamnose, arabinose, xylose, maltose, cellobiose, isomaltose, gentiobiose, lactose, lactulose, trehalose, isotrehalose, raffinose, maltotriose, maltotetraose, amylose, cellulose, chitin, amylopectin, glycogen and inulin. Still further examples are polyalcohols such as mannitol and sorbitol, diols and polyols such as poly(ethylene glycol) and poly(propylene glycol), water-soluble cellulosic polymers such as methyl cellulose, methylethylcellulose, hydroxyethylcellulose, hydroxypropylmethylcellulose, and sodium carboxymethylcellulose, and water-soluble polymers such as polyvinylpyrrolidone.

The particle or droplet size of the pore forming agent will be comparable to the diameter of the pores sought to be formed, and the quantity of pore forming agent will accordingly correspond to the total pore volume sought. The quantity may range from about 5% to about 95% of the total of polymer and pore forming agent, on a volume basis, although preferably from about 10% to about 60%, and more preferably from about 15% to about 40%.

In accordance with this invention, the porous hydrophobic material is the sole restriction to flow across the wall of the capsule. The porous hydrophobic material may thus be laminated with or supported by an additional lamina or support structure which is open to all types of fluid flow, such as an open-mesh or webbed structure, for purposes such as adding structural support if needed. Preferably, however, the porous hydrophobic material is the sole material separating the capsule interior from the surrounding environment.

As explained in further detail below, the porous hydrophobic material may comprise a section of the capsule wall or the entire wall, the choice depending on the configuration of the capsule reservoir and the number of compartments in the reservoir. When only a section of the capsule wall is porous hydrophobic material, that section will not contain the orifice from which the drug will be released, and will generally be at an opposite end of the capsule from that where the orifice is located. Also, when the capsule contains an osmotically active agent in addition to the drug and located in a region inside the capsule separate from the drug, the porous hydrophobic material will occupy at least part, and preferably all, of the section of the capsule wall adjacent to the region initially containing the osmotically active agent. In configurations of this type, the wall adjacent to the drug region is preferably substantially non-porous, or if porous, having pores of much smaller diameter and/or number such that any water permeability is at a slower rate than through the wall adjacent to the region of the separate osmotically active agent.

Osmotic drug delivery capsules in accordance with the present invention may be manufactured by a variety of techniques, many of which are described in the literature. In one such technique, the drug is prepared as a solid or semi-solid formulation and pressed into a pellet or tablet whose dimensions correspond to the internal dimensions of the capsule interior, or the portion or compartment of the capsule interior which will be occupied by the drug. The solid formulation may be a mixture of the drug and an osmagent or osmopolymer, or any other solid material which will form a cohesive pellet. Depending on the nature of the materials used, the drug and other solid ingredients may be processed prior to the pellet formation by such procedures as ballmilling, calendering, stirring or roll-milling to achieve a fine particle size and hence a fairly uniform mixture. For systems involving two or more zones in the capsule interior, such as those in which the drug and the osmagent or osmopolymer are in discrete compartments, the individual zones may be prepared and formed separately, then placed in contact and combined in a manner causing them to adhere, either directly or indirectly through a partition, using conventional multi-layer tablet pressing techniques.

Once the pellet has been formed, it is placed inside a pre-formed capsule. The capsule may be formed from any of the wall-forming materials disclosed above by the use of a mold, with the materials applied either over the mold or inside the mold, depending on the mold configuration. Alternatively, the capsule may be prepared by any of the wide variety of techniques known in the art for forming capsules used in the pharmaceutical industry.

The orifice is also formed by conventional techniques described in the literature. Included among these methods are mechanical drilling, laser drilling, and liquid techniques using an orifice forming agent, such as erosion, extraction, dissolving, bursting or leaching, depending on the nature of the agent used. The capsule will contain at least one such orifice, and in most configurations, one orifice will suffice. The dimensions of the orifice in terms of both diameter and length will affect the rate at which the drug is released from the capsule in response to the pressure differential resulting from the volumetric expansion of the capsule contents caused by the osmotic imbibition. The considerations involved in determining the optimum dimensions of the orifice for any particular capsule or drug are the same as those for orifices of capsules of the prior art, and selection of the appropriate dimensions will be readily apparent to those skilled in the art.

The functional components of the capsule will include the drug or other beneficial agent which the capsule is intended to deliver in a sustained manner, and the osmotically active compound, which as indicated above may assume any of various forms.

Species which fall within the category of osmagent, i.e., the non-volatile species which are soluble in water and create the osmotic gradient driving the osmotic inflow of water, vary widely. Examples are magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic. Examples are poly (hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally crosslinked with glyoxal, formaldehyde or glutaraldehyde and having a degree of polymerization of 200 to 30,000, a mixture of methyl cellulose, crosslinked agar and carboxymethylcellulose, a mixture of hydroxypropyl methylcellulose and sodium carboxymethylcellulose, polymers of N-vinyl lactams, polyoxyethylene-polyoxypropylene gels, polyoxybutylene-polyethylene block copolymer gels, carob gum, polyacrylic gels, polyester gels, polyurea gels, polyether gels, polyamide gels, polyimide gels, polypeptide gels, polyamino acid gels, polycellulosic gels, Carbopol® acidic carboxy polymers having molecular weights of 250,000 to 4,000,000, Cyanamer® polyacrylamides, crosslinked indene-maleic anhydride polymers, Good-Rite® polyacrylic acids having molecular weights of 80,000 to 200,000, Polyox® polyethylene oxide polymers having molecular weights of 100,000 to 5,000,000, starch graft copolymers, and Aqua-Keeps® acrylate polymer polysaccharides.

For capsules which include separate regions for the drug and the osmotic engine, the drug region may itself include an osmotically active agent such as an osmopolymer in addition to the drug to enhance volume expansion. Capsules in which this will produce a useful result will be those in which the drug region may not permit an osmotic inflow of water although free passage of water occurs across the interface between the regions, as well as those in which both regions permit an osmotic inflow of water, regardless of whether the interface permits transfer of water between the regions. The type or amount of osmotically active agent may differ between the two regions as a means of controlling or minimizing variations in the drug release rate, since the osmotically active agent in the drug region will be released along with the drug, and the rate at which the osmotic agents swell upon imbibition of water may vary with time. Considerations such as these are likewise familiar to those skilled in the art, and the appropriate selection of osmotically active agents may be made accordingly.

As indicated above, this invention is of particular interest as a means of providing osmotic drug delivery systems of entirely biodegradable materials, particularly those in which the capsule walls are of hydrophobic biodegradable polymers such as polymers of d-lactic acid, l-lactic acid, d,l-lactic acid, glycolic acid, and methylethylglycolic acid, copolymers of lactic and glycolic acids, poly(orthoesters) and copolymers of caprolactone and lactic acid. Osmotically active agents and water-swellable polymers appropriate for use with a biodegradable system will accordingly be agents which are biocompatible, biodegradable or excretable. Materials meeting this description will be readily apparent to those skilled in the art. Examples are sodium chloride, dextran, poly(vinylpyrrolidone), and hydroxypropylmethylcellulose. The materials included in the drug formulation to enhance the properties of the drug or its distribution in the host's system will likewise be biocompatible, biodegradable or excretable. Examples are binders such as poly(ethylene glycol), gelatin, agar, carboxyxellulose, poly(vinyl alcohol) and poly(vinyl pyrrolidone), and lubricants such as lecithin and other phospholipids, sesame oil and other vegetable oils, and stearic acid and salts of stearic acid such as aluminum stearate, magnesium stearate and zinc stearate, as well as combinations of the species from two or more of these groups.

While the term "drug" is used extensively throughout this specification, the use of this term has been primarily for purposes of convenience. The present invention applies to the administration of beneficial agents in general, which include any physiologically or pharmacologically active substance that produces a local or systemic effect. Agents that can be delivered according to this invention are those that are compatible with the polymeric matrix and with the required excipient. Included among the types of agents which meet this description are biocides, sterilization agents, food supplements, nutrients, vitamins, sex sterilants, fertility inhibitors and fertility promoters. The agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, analgesics, local anesthetics, antibiotic agents, anti-inflammatory corticosteroids, ocular drugs and synthetic analogs of these species.

Examples of beneficial agents which this invention can be utilized with are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17 β-estradiol, ethinyl estradiol, ethinyl estradiol 3-methyl ether, pednisolone, 17 β-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hoemone, follicle stimulating hormone, chorionic gonadotropin; gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The active agent can be present in this invention in a wide variety of chemical and physical forms, such as uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations can be used. Derivatives such as esters, ethers and amides can be used. An active agent can be used alone or mixed with other active agents.

The lists of active agents recited above are given only to illustrate the types of active agents which are suitable for use in practicing the invention, and are not intended to be exhaustive.

The amount of active agent employed in the delivery device will be that amount necessary to deliver a therapeutically effective amount of the agent to achieve the desired result at the site of application. In practice, this will vary depending on the particular agent, the severity of the condition, and the desired effect, as well as the desired rate and duration of release.

Animals to whom drugs may be administered using systems of this invention include humans and other mammals and warm-blooded animals in general, avians, reptiles and fishes. Household animals, sport animals, farm animals, laboratory animals and zoo animals are included. The invention is of particular interest for application to humans and household, sport and farm animals, particularly mammals. Prominent examples other than humans are sheep, goats, cattle, horses and pigs.

DETAILED DESCRIPTION OF THE DRAWINGS

The drawings appended to this specification represent three configurations of osmotic delivery systems (i.e., "osmotic pumps") constructed in accordance with this invention.

FIG. 1 depicts an elementary osmotic pump, which is the simplest design of the three. The pump is in the form of a generally cylindrical capsule 11, the enclosure of which consists of a capsule wall 12 forming the sides and one end of the capsule, and a cap 13 closing off the remaining end of the capsule. The cap contains a single orifice 14, and the capsule contains a single interior reservoir 15. Contained in the reservoir are a formulation which includes the drug, an osmagent such as sodium chloride, for example, and optionally an osmopolymer as well. The capsule wall 11 is formed of porous hydrophobic material such as poly(d,l-lactic acid) or a copolymer of d,l-lactic and glycolic acids, and the end cap is formed of the same material but nonporous. Imbibition of water through the capsule wall 12 results in drug, osmagent and osmopolymer (if included) being forced out through the orifice 14.

Figure 2:
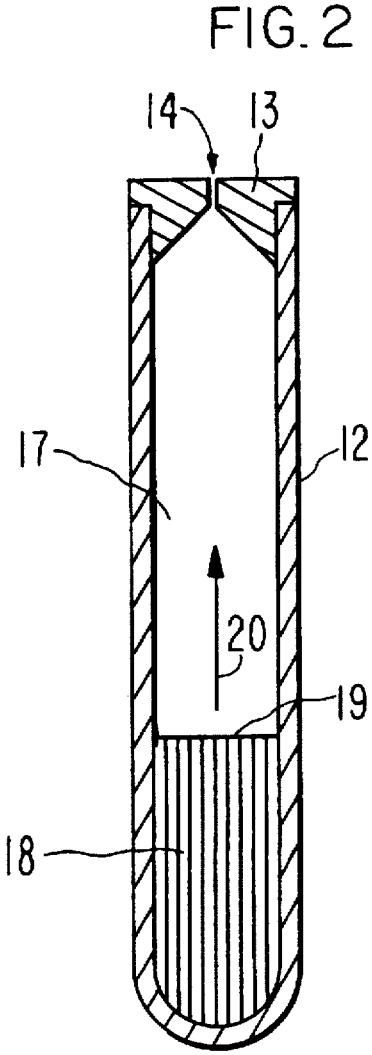
FIG. 2 is a cross section of a second osmotic device as a further implementation of the invention, incorporating a feature not present in the device of FIG. 1.

FIG. 2 depicts a pump referred to as a "push-pull" osmotic pump. The capsule 11 is the same as that of the elementary osmotic pump of FIG. 1, with a single continuous wall 12 of porous hydrophobic material, and an end cap 13 of the same material in nonporous form with a single orifice 14. The drug and the osmotically active compound, however, are largely, if not entirely, immiscible, and form two separate phases 17, 18, respectively, separated by an interface 19. The lower phase 18, which contains the osmotically active compound, expands as a result of the osmotic inflow of water, driving the interface upward in the direction of the arrow 20, forcing the drug in the upper phase 17 out the orifice 14.

Figure 3:
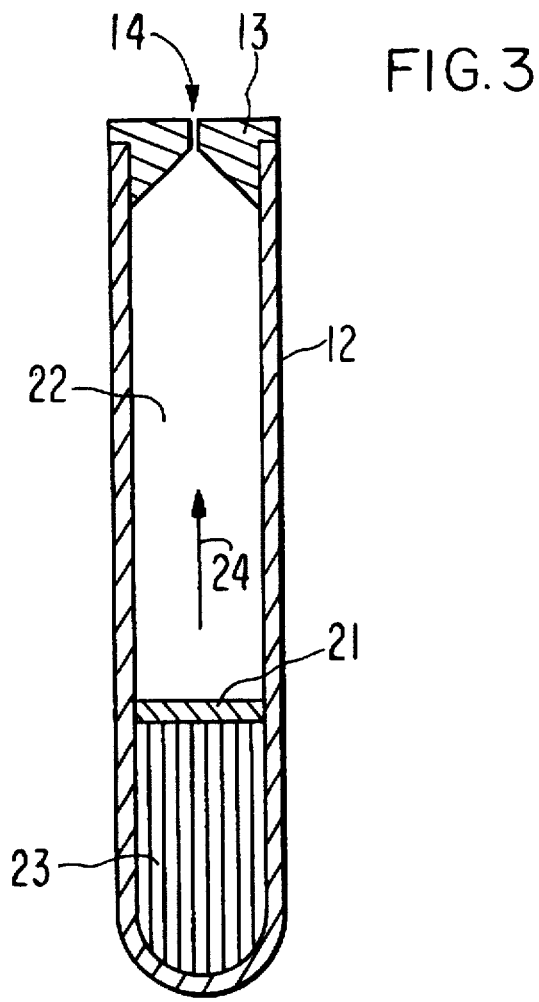
FIG. 3 is a cross section of a third osmotic device as a still further implementation of the invention.

FIG. 3 depicts a second version of the push-pull pump. In this version, the capsule interior however contains a piston 21, which divides the interior space into two compartments 22, 23. The piston is a barrier which does not permit the passage of fluid between the two compartments, but which is capable of movement up the capsule, in the direction indicated by the arrow 24. Here as in FIG. 2, the compartment nearest the orifice 14 is the drug compartment 22, while the compartment furthest from the orifice is the osmotic engine compartment 23. The latter contains the osmotically active compound, and the expansion resulting from the osmotic inflow of water into the osmotic engine compartment 23 drives the piston 21 upward, forcing the drug in the drug compartment 22 out the orifice 14.

The drug compartment will most likely also experience an osmotic inflow of water since the wall surrounding the two compartments is the same porous material. This can be controlled however by controlling the composition of the drug formulation, either to suppress any expansion occurring in the drug compartment or to promote it.

Figure 4:
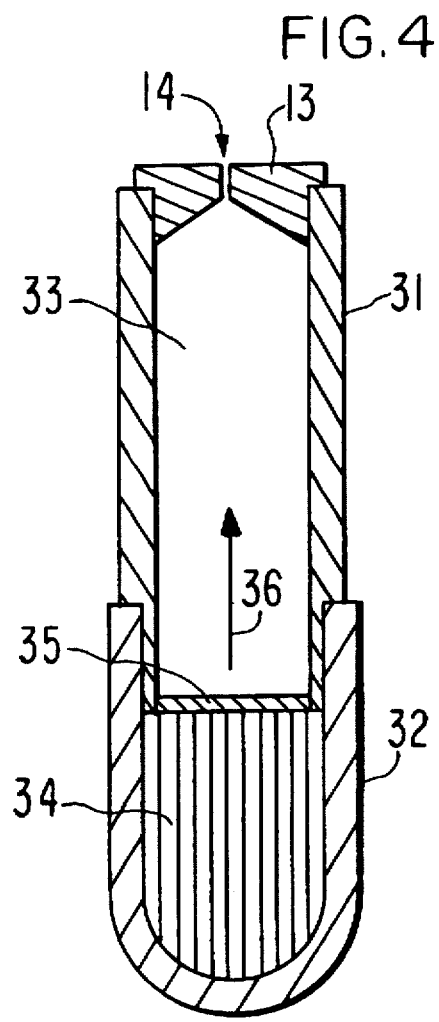
FIG. 4 is a cross section of a fourth osmotic device representing yet another implementation of the invention.

The pump depicted in FIG. 4 is a further variation on the push-pull pump of FIG. 2. Here the capsule wall is in two sections 31, 32, one section being nearest the orifice 14 and surrounding the drug compartment 33, and the other section being furthest from the orifice 14 and surrounding the osmotic engine compartment 34. A piston 35 separates the two compartments in the same manner as the piston 21 of FIG. 3.

The distinction between the two wall sections is that only the osmotic engine compartment section 34 is porous, the two sections otherwise being of the same material. Osmotic inflow is thereby limited to the osmotic engine compartment section 34. Likewise, any potential for leakage of the drug from the capsule other than through the orifice 14 is eliminated. This construction is particularly useful for drugs which either might pass through a porous wall of hydrophobic material or are unstable when exposed to an aqueous environment.

The initial position of the piston, prior to implantation or ingestion of the pump for purposes of drug delivery, is at the lower end of the nonporous wall section 31, as shown in the drawing. As osmotic inflow of water to the osmotic engine compartment 34 proceeds, the resulting expansion of the contents of that compartment causes the piston 35 to move in the direction of the arrow 36, forcing the drug in the drug compartment 33 out the orifice 14.

The following examples are offered for purposes of illustration, and are intended neither to limit nor to define the invention in any manner.

EXAMPLE 1

This example illustrates the fabrication of a delivery system in accordance with the present invention, the system containing a semipermeable membrane, a driving system, and an exit port.

First, glucose is milled to a no. 230 size mesh screen. The milled glucose (15 g) is then mixed with poly-(d,l-lactide) (35 g, 200,000 average molecular weight), and the mixture is milled for about an hour. The milled blend is then passed through a grinding mill. A quantity of the resulting particles (1.15 g) is then placed in a transfer mold where the particles are molded into the form of a membrane cup with an open end. The dimensions of the membrane cup are 1.015–1.02 in (2.578–2.591 cm) in length, with an inside diameter of 180 mil (0.457 cm) and a wall thickness of 25–30 mil (0.0635–0.0762 cm) wall thickness. The membrane cup is placed in water with other membrane cups similarly prepared, and stirred at 37° C. The water is changed after 3, 7, and 10 days. The membrane cups are removed after 14 days, then cleaned with 70% ethanol/30% water, followed by water. The membrane cups are then placed in a vacuum chamber for 48 hours at a maximum of 200 millitorr. The result are bioerodible, semipermeable membrane cups.

Next, sodium chloride is milled to a no. 230 size mesh screen. To the milled sodium chloride (19.8 g) is added magnesium stearate (0.2 g), and the mixture blended for 10 minutes to produce a homogenous expandable driving composition. Once formed, the composition is pressed into osmotically active tablets in a tablet press at a pressure of 1000 lb to produce a 650 mg cylindrical osmotically active expandable tablet with one flat and one convex end and with a diameter of about 180 mil to conform to the inner shape of the membrane cup.

Next, the exit cap for the device is formed. This is done by placing poly-(d,l-lactide) (1 g) in a transfer mold where it is molded into the form of an exit cap. An orifice of 0.010 in (0.0254 cm) diameter is then drilled through the cap.

A poly-(d,l-lactide) glue is made by mixing together poly-(d,l-lactide) (650 mg) and acetone (5 mL).

The driving system is then assembled by insertion of the osmotically active tablet into the semipermeable membrane cup, followed by applying the poly-(d,l-lactide) glue to the mating surface of the exit cap, then fully inserting the cap into the open end of the membrane cup, and finally twisting the cap to ensure full contact of both parts with the glue.

EXAMPLE 2

This example illustrates the preparation of a delivery system for the delivery of hydrocortisone in accordance with the present invention.

A poly-(d,l-lactide) semipermeable membrane cup, poly-(d,l-lactide) glue, and an exit cap are prepared as described in Example 1.

Sodium chloride is milled to a no. 230 size mesh screen. To the milled sodium chloride (17.8 g) is added sodium carboxymethylcellulose (0.2 g) and hydrocortisone (2.0 g), and the mixture is blended for 10 minutes to produce a homogenous, drug-containing, expandable driving composition. The composition is pressed into drug-containing osmotically active tablets in a tablet press at 1000 lb to produce a 650 mg cylindrical tablet with one flat and one convex end conforming to the inside shape of the membrane cup. The semipermeable membrane, the exit cap, and the drug-containing osmotically active tablets are joined as in Example 1.

EXAMPLE 3

This example illustrates the preparation of a delivery system for the delivery of betamethasone in accordance with the present invention.

A poly-(d,l-lactide) semipermeable membrane cup, poly-(d,l-lactide) glue, and an exit cap are prepared as described in Example 1.

A mixture of betamethasone phosphoric acid (1.52 g), betamethasone disodium phosphate (1.37 g) and magnesium stearate (29 mg) is blended for 10 minutes to produce a homogenous, drug-containing, expandable driving composition. Once formed, the composition is pressed into a drug-containing osmotically active tablet in a tablet press at 1000 lb to produce a 500 mg cylindrical tablet with one flat and one convex end shaped to fit into the membrane cup. The semipermeable membrane cup, the exit cap, and the drug-containing osmotically active tablets are joined as in Example 1.

EXAMPLE 4

This example illustrates the preparation of another delivery system in accordance with the invention for delivery of hydrocortisone.

A poly-(d,l-lactide) semipermeable membrane cup and poly-(d,l-lactide) glue are prepared as described in Example 1. The membrane cup has a length of 2.2 cm, an internal diameter of 190 mil and a wall thickness of 30 mil.

Sodium chloride is milled to no. 230 size mesh screen. To the milled sodium chloride (6 g) is added sodium carboxymethylcellulose (4 g), and the mixture is blended for 10 minutes to produce a homogenous expandable driving composition. The composition once formed is pressed into an osmotically active tablet in a tablet press at a pressure of 1000 lb to produce a 100 mg cylindrical tablet with one flat and one convex end shaped to fit inside the membrane cup.

Next, a gram of poly-(d,l-lactide) is formed into an exit cap with an orifice of 0.030 inch (0.076 cm), using the procedures described above.

An inert spacer or piston is formed by combining ultrathene (0.5 g) and vynathene (0.5 g), mixing the combination for 10 minutes, and placing the mixture in a transfer mold shaped to provide the piston with a diameter of about 190 mil (0.483 cm) and a thickness of about 200 mil.

The drug composition is then formed by combining glycerol (10 g), hydrocortisone (14.25 g) and lecithin (25.75 g), and milling the mixture for about 20 minutes.

The device is assembled by first inserting the osmotically active tablet into the semipermeable membrane cup, then inserting the inert spacer over the tablet. This is followed by injecting 180 mg of the drug composition into the semipermeable membrane cup through a syringe. The poly-(d,l-lactide) glue is then added to the mating surface of the exit cap, and the cap is fully inserted into the open end of the membrane cup and twisted to ensure secure contact.

EXAMPLE 5

This example illustrates a determination of the in vitro release rate of sodium chloride from devices in accordance with this invention.

Four devices prepared according to the description in Example 1 were individually placed in a container and submerged in distilled water at 37° C. The water was replaced at regular time intervals, and the removed water was analyzed for its sodium chloride content. The analyses showed that after an initial startup period, all of the devices released sodium chloride at a continuous rate of between 0.3 mg/h and 0.4 mg/h for 400 hours.

EXAMPLE 6

This example illustrates a determination of the in vivo release rate of sodium chloride from devices in accordance with this invention.

Figure 5:
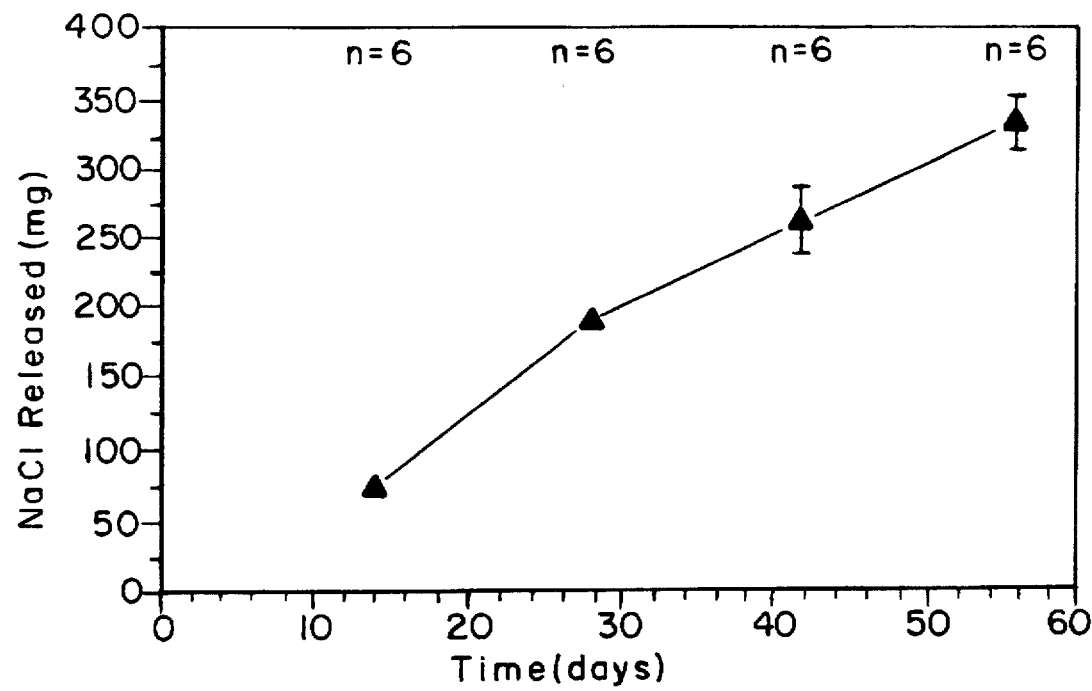
FIG. 5 is a plot of the amount of a test species released in vivo from a delivery device in accordance with this invention, as a function of time.

Devices prepared in accordance with Example 1 were implanted subcutaneously in rats and left for 14, 28, 42 or 56 days. Replicates were conducted for each time period. At the end of each time period, the devices were explanted from the rats. The devices were then emptied to remove any material remaining, and the material was analyzed for sodium chloride content as indicated by conductivity, to determine the amount of sodium chloride released from the device into the rat. The results are shown in FIG. 5, from which it is clear that the NaCl was released at a substantially steady rate (as indicated by a line of substantially constant slope representing milligrams vs. days) over the entire time period of the test.

EXAMPLE 7

This example illustrates a determination of the in vitro release rate of hydrocortisone from devices in accordance with this invention.

Figure 6:
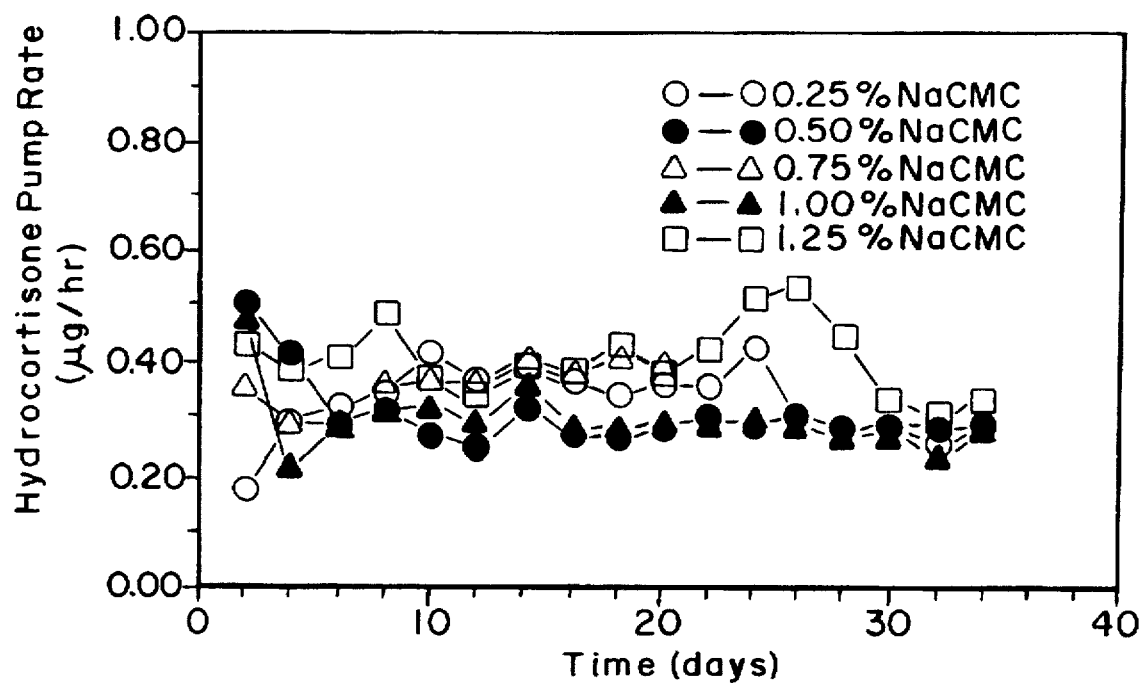
FIG. 6 is a plot of release rate vs. time for an in vitro experiment using a device in accordance with this invention.

Devices were prepared according to Example 2, the drug compositions of all of the devices containing 10 weight percent hydrocortisone but with differing amounts of sodium carboxymethylcellulose (NaCMC), ranging from 0.25 weight percent to 1.25 weight percent. The procedures of Example 5 were followed, with the devices being transferred to fresh media every 48 hours. The media were analyzed for hydrocortisone content by UV absorbance. The results, expressed in terms of the release rate (micrograms per hour) vs. time (days), are shown in FIG. 6, which demonstrates a substantially steady release rate at all NaCMC concentrations.

EXAMPLE 8

This example illustrates a determination of the in vitro release rate of hydrocortisone from further devices in accordance with this invention.

Figure 7:
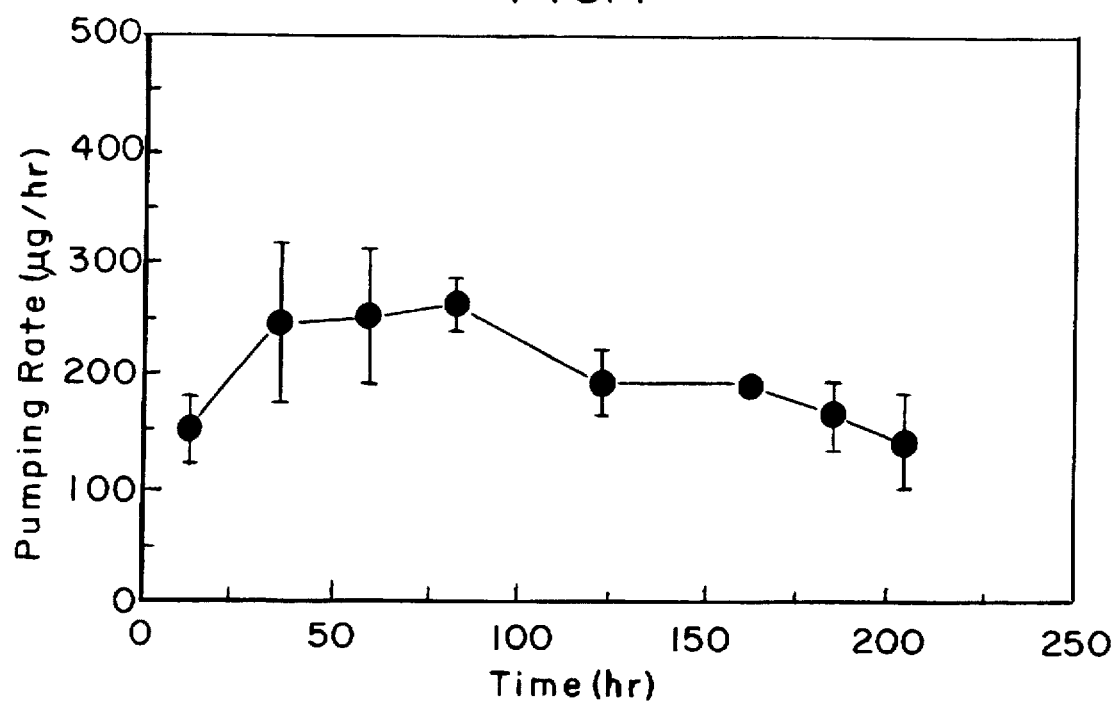
FIG. 7 is a further plot of release rate vs. time for an in vitro experiment using a device in accordance with this invention.

Devices were prepared according to Example 4, with a drug composition of 24.1 weight percent hydrocortisone, 56.4 weight percent lecithin and 19.5 weight percent glycerol. The piston was constructed of silicone rubber. The procedures of Example 5 were followed, with the devices being transferred to fresh media every 48 hours. The media were analyzed for hydrocortisone content by UV absorbance. The results, expressed in terms of the release rate (micrograms per hour) vs. time (hours), are shown in FIG. 7, which demonstrates a substantially steady release rate.

EXAMPLE 9

This example illustrates a determination of the in vitro release rate of betamethasone from devices in accordance with this invention.

Figure 8:
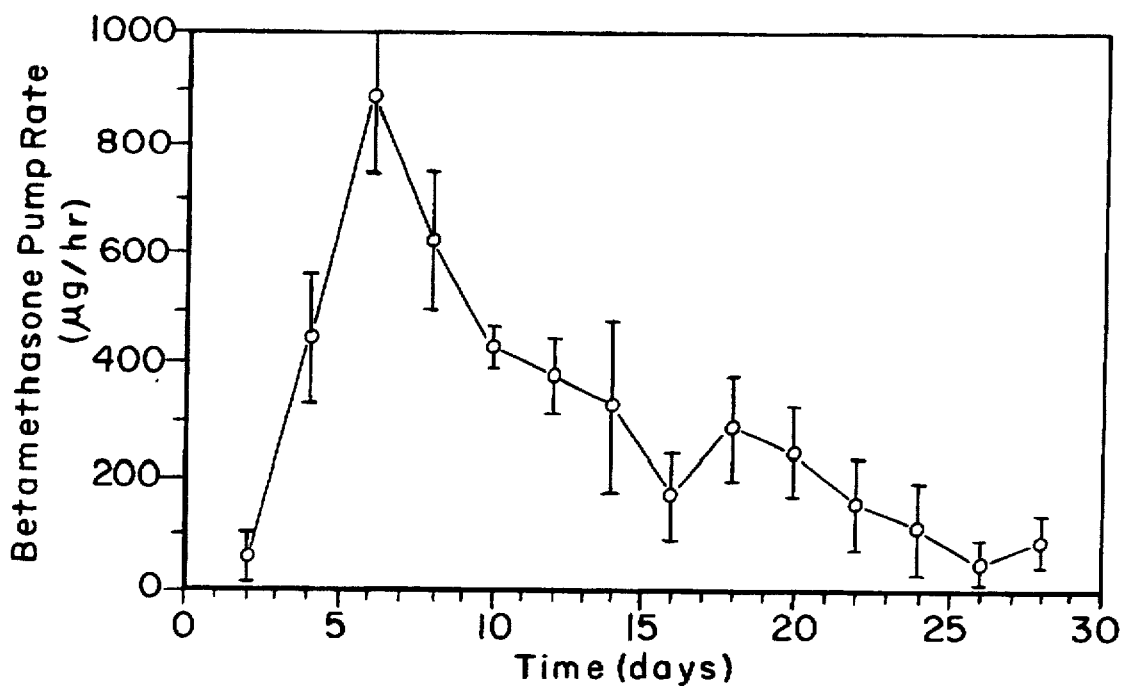
FIG. 8 is a still further plot of release rate vs. time for an in vitro experiment using a device in accordance with this invention.

Devices were prepared according to Example 3. The procedures of Example 5 were followed, with the devices being transferred to fresh media every 48 hours. The media were analyzed for betamethasone content by UV absorbance. The results, expressed in terms of release rate vs. time, are shown in FIG. 8.

The foregoing is offered primarily for purposes of illustration. It will be readily apparent to those skilled in the art that the materials, dimensions, manufacturing procedures and other parameters of the system may be further modified or substituted in various ways without departing from the spirit and scope of the invention.

What is claimed is:

1. An osmotically driven device for lodgment in an aqueous environment in the interior of an animal for the controlled delivery of a beneficial agent to said animal, said device comprising:
    (a) a beneficial agent;
    (b) an osmotically active substance which expands on exposure to water in the aqueous environment; and
    (c) a wall, surrounding said agent and said substance, and defining an exit orifice for releasing said agent therethrough in response to expansion of said substance; said wall being formed of a non-wetting hydrophobic material which material is a biodegradable polymer selected from the group consisting of poly (lactic acid), poly (glycolic acid), and copolymers of lactic acid and glycolic acid, and at least a section of said wall having air-filled interconnected pores therethrough, through which pores water vapor from the aqueous environment passes into the substance, said wall section being impermeable to liquid water and permeable to water vapor.

2. An osmotically driven device in accordance with claim 1 in which said pores are from 0.01 micron to 1000 microns in diameter.

3. An osmotically driven device in accordance with claim 1 in which said pores are from 0.1 micron to 500 microns in diameter.

4. An osmotically driven device in accordance with claim 1 in which said pores are from 3 microns to 300 microns in diameter.

5. An osmotically driven device in accordance with claim 1 in which said pores are from 30 microns to 100 microns in diameter.

6. An osmotically driven device in accordance with claim 1 in which said osmotically active substance is a material selected from the group consisting of a water-swellable hydrophilic polymer, water-soluble salts, water-soluble saccharides, and combinations thereof.

7. An osmotically driven device in accordance with claim 1 in which said beneficial agent and said osmotically active substance are combined in a single mixture.

8. An osmotically driven device in accordance with claim 1 in which said wall consists essentially of said porous wall section.

9. An osmotically driven device in accordance with claim 1 further comprising a movable fluid-impermeable barrier dividing said beneficial agent and said osmotically active substance.

10. An osmotically driven device in accordance with claim 1 wherein said wall comprises a first and second wall sections, said first wall section being formed of said porous hydrophobic material and said first wall section surrounding said osmotically active substance.

11. An osmotically driven device in accordance with claim 10 in which said second wall section is formed of non-porous fluid impermeable material.

12. An osmotically driven device in accordance with claim 10 in which said first and second wall sections comprise a polymer selected from the group consisting of poly(lactic acid), poly(glycolic acid), and copolymers of lactic acid and glycolic acid, said first wall section defining pores of diameter ranging from 3 microns to 300 microns, and said second wall section being formed of nonporous, impermeable material.

* * * * *